(12) United States Patent
Nitta et al.

(10) Patent No.: US 12,275,690 B2
(45) Date of Patent: Apr. 15, 2025

(54) METHOD FOR PRODUCING ISOCYANATE COMPOUND

(71) Applicant: SUMITOMO CHEMICAL COMPANY, LIMITED, Tokyo (JP)

(72) Inventors: Hirohisa Nitta, Takarazuka (JP); Yuta Nagashima, Takarazuka (JP); Hiroki Maruyama, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 723 days.

(21) Appl. No.: 17/637,905

(22) PCT Filed: Aug. 21, 2020

(86) PCT No.: PCT/JP2020/031699
§ 371 (c)(1),
(2) Date: Feb. 24, 2022

(87) PCT Pub. No.: WO2021/039660
PCT Pub. Date: Mar. 4, 2021

(65) Prior Publication Data
US 2022/0274915 A1    Sep. 1, 2022

(30) Foreign Application Priority Data
Aug. 29, 2019 (JP) .................. 2019-156453

(51) Int. Cl.
*C07C 263/10* (2006.01)
*C07D 257/04* (2006.01)

(52) U.S. Cl.
CPC .......... *C07C 263/10* (2013.01); *C07D 257/04* (2013.01)

(58) Field of Classification Search
CPC ........................... C07C 263/10; C07D 257/04
See application file for complete search history.

(56) References Cited

U.S. PATENT DOCUMENTS

| | | | |
|---|---|---|---|
| 3,465,023 | A | 9/1969 | Kamal |
| 3,852,317 | A | 12/1974 | Zanker |
| 10,479,780 | B2 | 11/2019 | Ebike et al. |
| 2004/0082701 | A1 | 5/2004 | Koch et al. |
| 2015/0051171 | A1 | 2/2015 | Yoshimoto et al. |
| 2017/0342023 | A1 | 11/2017 | Yoshimoto et al. |
| 2018/0354894 | A1 | 12/2018 | Miyamoto et al. |
| 2018/0362509 | A1 | 12/2018 | Ebike et al. |

FOREIGN PATENT DOCUMENTS

| | | |
|---|---|---|
| JP | 48-57919 A | 8/1973 |
| JP | 60-255758 A | 12/1985 |
| JP | 2004-123746 A | 4/2004 |
| JP | 2014-80415 A | 5/2014 |
| JP | 2016-113426 A | 6/2016 |
| WO | WO 2013/162072 A1 | 10/2013 |
| WO | WO 2016/098561 A1 | 6/2016 |
| WO | WO 2017/104709 A1 | 6/2017 |

OTHER PUBLICATIONS

Extended European Search Report dated Aug. 16, 2023 for Application No. 20859500.9.
Chinese Office Action and Search Report for corresponding Chinese Application No. 202080059829.2, dated Dec. 6, 2022, with English translation.
English translation of the International Preliminary Report on Patentability and Written Opinion of the International Searching Authority for International Application No. PCT/JP2020/031699, dated Mar. 10, 2022.
English translation of the International Search Report for International Application No. PCT/JP2020/031699, dated Oct. 6, 2020.
Lau et al., "New β-Alanine Derivatives Are Orally Available Glucagon Receptor Antagonists," Journal of Medical Chemistry, vol. 50, No. 1, 2007, pp. 113-128 (16 pages total).
Chinese Office Action for Chinese Application No. 202080059829.2, dated Apr. 18, 2023, with English translation.
Indian Office Action for Indian Application No. 202247013323, dated Dec. 27, 2023, with an English translation.

*Primary Examiner* — Deborah D Carr
(74) *Attorney, Agent, or Firm* — Birch, Stewart, Kolasch & Birch, LLP

(57) ABSTRACT

The present specification discloses a method for producing an isocyanate compound. The invention relates to a method for producing the compound represented by formula (2),

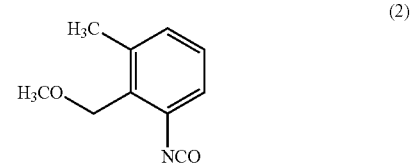

wherein the compound represented by formula (1)

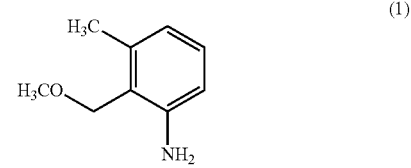

or a salt thereof is mixed with phosgene(s) under a condition such that the pH of the aqueous layer is 1 or less, in the presence of a water-immiscible solvent and water.

9 Claims, No Drawings

METHOD FOR PRODUCING ISOCYANATE COMPOUND

TECHNICAL FIELD

This patent application claims priority under the Paris Convention based on Japanese Patent Application No. 2019-156453 (filed on Aug. 29, 2019), which is incorporated herein by reference in its entirety.

The present specification discloses a method for producing an isocyanate compound.

BACKGROUND ART

The compound represented by formula (2)

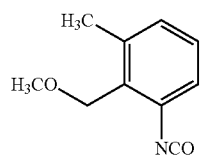

(2)

(having a compound name of 3-methyl-2-(methoxymethyl)-1-isocyanatobenzene, hereinafter referred to as compound (2)) is useful as an intermediate for agrochemicals. For example, Patent Document 1 describes in Reference Manufacture Example 18 that the compound represented by formula (2) is produced by stirring a mixture of the compound (1)

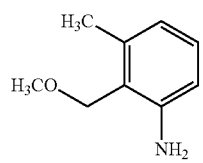

(1)

(having a compound name of 3-methyl-2-(methoxymethyl) aniline, hereinafter referred to as compound (1)), triphosgene, saturated sodium bicarbonate and ethyl acetate under ice-cold conditions.

PRIOR ART DOCUMENTS

Patent Documents

Patent Document 1: International Publication No. 2013/162072

SUMMARY OF INVENTION

Technical Problem

However, the production method described in Patent Document 1 was not satisfactory as an industrial production method in terms of yield. It is an object of the present invention to provide a method for producing the compound (2) in a high yield.

Solution to Problem

The present inventors have conducted intensive studies on the above problem and found the following method.

That is, the present invention encompasses the following preferred embodiments.

[1] A method for producing the compound represented by formula (2)

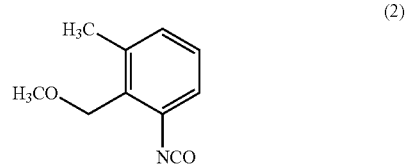

(2)

by reacting the compound represented by formula (1) with phosgenes to obtain the compound represented by formula (2),
wherein, in the presence of a water-immiscible solvent and water, the compound represented by formula (1)

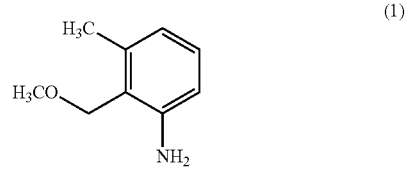

(1)

or its salt and the phosgenes are mixed under a condition such that an aqueous layer has a pH of 1 or less.

[2] The method according to [1], wherein the aqueous layer has a concentration of hydrogen chloride of 15% by weight or less.

[3] The method according to [2], wherein a base is added such that the aqueous layer has a concentration of hydrogen chloride of 15% by weight or less.

[4] The method according to [3], wherein the base is an alkali metal hydroxide.

[5] The method according to any of [1] to [4], wherein the phosgenes correspond to phosgene.

[6] The method according to any of [1] to [5], wherein the compound or salt thereof represented by formula (1) is a hydrochloride salt of the compound represented by formula (1).

[7] The method according to any of [1] to [6], further comprising a step of separating a mixture of an organic layer containing the compound represented by formula (2) and the aqueous layer obtained by the reaction to obtain the organic layer containing the compound represented by formula (2), and a step of dehydrating the organic layer at 50° C. or lower.

[8] A method for producing a compound represented by formula (3)

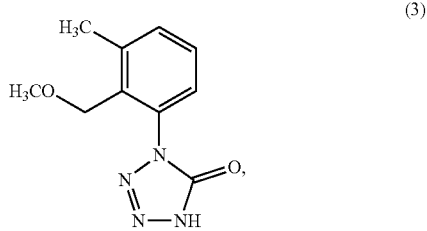

(3)

comprising the following steps:

Step 1 of producing the compound represented by formula (2)

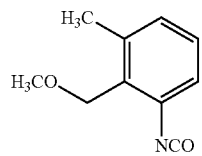

(2)

by reacting the compound represented by formula (1)

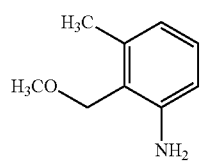

(1)

with phosgene to obtain the compound represented by formula (2), wherein, in the presence of a water-immiscible solvent and water, a salt of the compound represented by formula (1), phosgene and an alkali metal hydroxide are mixed under a condition such that an aqueous layer has a pH of 1 or less and the aqueous layer has a concentration of hydrogen chloride of 15% by weight or less;

Step 2 of obtaining an organic layer containing the compound represented by formula (2) from the mixture of an organic layer containing the compound of formula (2) and an aqueous layer obtained in Step 1, and dehydrating the organic layer at 50° C. or lower; and Step 3 of reacting the compound represented by formula (2) obtained in step 2 with an azide.

[9] A method for producing a compound of formula (4)

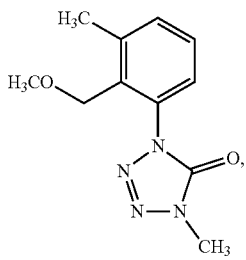

(4)

comprising, in addition to the Step 1, the Step 2 and the Step 3 recited in claim 8, a further step of methylating the obtained compound of formula (3).

Effect of the Invention

According to the present invention, it is possible to produce 3-methyl-2-(methoxymethyl)-1-isocyanatobenzene in a high yield.

MODES FOR CARRYING OUT THE INVENTION

The method for producing the compound (2) will be described.

The compound (2) can be produced by mixing the compound (1) or its salt with phosgenes in the presence of a water-immiscible solvent and water under a condition such that the pH of the aqueous layer is 1 or less. The compound (2) obtained by the invention will be converted into a by-product with a urea structure when further reacted with the compound (1) which is a raw material. If the compound (1) is mixed with phosgenes under the condition that the pH of the aqueous layer is 1 or less, the compound (2), which is a reaction product, is distributed to the organic layer, and the compound (1), which is a reaction raw material, is distributed to the aqueous layer as a hydrochloride salt, and the contact between the compound (1) and the compound (2) is suppressed. Therefore, it is assumed that the formation of by-products having the above urea-structure can be suppressed.

Solvents used in the reaction which are immiscible with water are those which are not decomposed by hydrogen chloride, such as aromatic hydrocarbons such as toluene, xylene and ethylbenzene; halogenated aromatic hydrocarbons such as chlorobenzene; aliphatic hydrocarbons such as hexane, heptane and cyclohexane; and mixtures of these. Toluene, ethylbenzene and xylene are preferred. The amount of solvent used is from 0.5 to 10 times the weight of the compound (1).

The amount of water used is from 0.5 to 10 times the weight of the compound (1).

Phosgenes include phosgene, diphosgene and triphosgene, and preferred is phosgene. The amount used is from 0.95 to 1.5 molar times, preferably from 1.0 to 1.3 molar times, the phosgene units to the compound (1).

The compound (1) or its salt can be obtained by the method described in International Publication No. 2013/162072. In order to keep the pH of the aqueous layer to be 1 or less from the initial stage of contact between the compound (1) or its salt and the phosgenes, it is preferable to use the salt of the compound (1) as a hydrochloride salt in the present invention. The hydrochloride salt may be produced in advance by reacting the compound (1) with hydrogen chloride, or it may be generated in the reaction system. The formation of the hydrochloride salt of the compound (1) in the reaction system can be achieved, for example, by adding the compound (1) to a mixture of a water-immiscible solvent and water containing hydrogen chloride; or by adding phosgenes to a mixture of a water-immiscible solvent and water and then reducing the pH of the aqueous layer to 1 or less, followed by adding the compound (1) and phosgenes while the pH of the aqueous layer being maintained at 1 or less.

Examples of the method for adding a water-immiscible solvent, water or water containing hydrogen chloride, the compound (1) or the hydrochloride thereof, and phosgenes include the following methods:

a method of adding phosgenes after adding a hydrochloride salt of the compound (1) to a mixture of a water-immiscible solvent and water;

a method of simultaneously adding a hydrochloride salt of the compound (1) and phosgenes to a mixture of a water-immiscible solvent and water;

a method of adding a hydrochloride salt of the compound (1) after adding phosgenes to a mixture of a water-immiscible solvent and water;

a method of adding phosgenes after adding the compound (1) to a mixture of a water-immiscible solvent and water containing hydrogen chloride; and a method of adding phosgenes to a mixture of a water-immiscible solvent and water to reduce the pH of the aqueous layer to 1 or less, and then adding the compound (1) and phosgenes while maintaining the pH of the aqueous layer to 1 or less.

A method of adding the compound (1) and phosgenes while maintaining the pH of the aqueous layer at 1 or less will be specifically described below as an example.

For example, the compound (1) and phosgenes of 0.5 mol times or more (total of phosgenes added to reduce the pH of the aqueous layer to 1 or less) in phosgene units with respect to the compound (1) are simultaneously and gradually added, with further adding phosgenes as needed; the compound (1), and phosgenes of 0.5 mol times or more (total of phosgenes added to reduce the pH of the aqueous layer to 1 or less) in phosgene units with respect to the compound (1) are added in small amounts alternately, with further adding phosgenes as needed.

Upon addition of phosgenes, the hydrogen chloride concentration in the aqueous layer increases accordingly. In order to suppress decomposition of the hydrochloride of the compound (1) or the compound (2) by a high concentration of hydrogen chloride, the hydrogen chloride concentration of the aqueous layer is preferably suppressed to 15% by weight or less. In order to suppress the hydrogen chloride concentration in the aqueous layer, water may be added to dilute it, or a base may be added to neutralize a part of hydrogen chloride. From the viewpoint of productivity, it is preferable to add a base to neutralize a part of hydrogen chloride.

The concentration of hydrogen chloride in the aqueous layer may be measured, or calculated using the value obtained by dividing the weight of hydrogen chloride (stoichiometric amount) generated from the hydrochloride of the compound (1) and phosgenes by the theoretical weight of the aqueous layer. When a base is added, it may be calculated by using the value obtained by dividing the value obtained by subtracting the amount of hydrogen chloride neutralized by the base from the weight of hydrogen chloride (stoichiometric amount) generated from the hydrochloride of the compound (1) and phosgenes by the theoretical weight of the aqueous layer.

Examples of the base include alkali metal hydroxides such as sodium hydroxide and potassium hydroxide.

Examples of the order in which the compound (1), phosgenes, and a base are added to a mixture of water-immiscible solvent and water include the following methods:

a method of adding 0.05 to 0.1 mol times phosgenes in phosgene units to the compound (1) such that the pH of the aqueous layer is 1 or less, and then adding 0.4 to 0.7 mol times phosgenes in phosgene units and the compound (1) simultaneously and gradually, followed by simultaneous and gradual addition of 0.3 to 0.9 mol times phosgenes in phosgene units and a base to the mixture so that the hydrogen chloride concentration in the aqueous layer is 15% by weight or less; or a method of adding 0.05 to 0.1 mol times phosgenes in phosgene units to the compound (1) such that the pH of the aqueous layer is 1 or less, and then adding 0.3 to 0.5 mol times phosgenes in phosgene units and 25 to 40 mol % of the compound (1) simultaneously and gradually, followed by simultaneous and gradual addition of 0.7 to 0.9 mol times phosgenes in phosgene units and 65 to 75 mol % of the compound (1) and a base such that the hydrogen chloride concentration in the aqueous layer is 15% by weight or less.

When the hydrochloride salt of the compound (1) remains in the aqueous layer, phosgenes can be further added.

The reaction temperature is usually −10° C. to 40° C., preferably 0 to 20° C.

After completion of the reaction, the organic layer containing the compound (2) and the aqueous layer are separated. Since the separated organic layer contains water and is unstable, it is necessary to be quickly dehydrated. Examples of the method of dehydration include adsorption by molecular sieves and concentration. From an economical point of view, concentration is preferable, and from the viewpoint of stability of the compound (2), dehydration at 50° C. or less under reduced pressure is more preferable.

The organic layer containing the dehydrated compound (2) can be used, for example, in the production of a tetrazolinone compound useful as an intermediate for agrochemicals.

The method will be explained in which the compound represented by the formula (4) (hereinafter, also referred to as compound (4)) is produced from the obtained compound (2) via the compound represented by the formula (3) (hereinafter, also referred to as compound (3)).

The compound (3) can be produced by reacting the compound (2) with an azide to cyclize it.

Examples of the solvent that can be used in the reaction include hydrocarbons such as n-heptane, n-hexane, cyclohexane, n-pentane, toluene, xylene, and ethylbenzene, ethers such as tetrahydrofuran, 1,4-dioxane, ethylene glycol-dimethyl ether, anisole, methyl tert-butyl ether and diisopropyl ether, halogenated hydrocarbons such as chlorobenzene and ortho-dichlorobenzene, acid amides such as N,N-dimethylformamide, 1,3-dimethyl-2-imidazolidinone, and N-methylpyrrolidone, sulfoxides such as dimethyl sulfoxide, nitriles such as acetonitrile and propionitrile, and mixtures thereof, preferably acid amides such as N,N-dimethylformamide, 1,3-dimethyl-2-imidazolidinone and N-methylpyrrolidone, more preferably N,N-dimethylformamide.

Examples of the azide that can be used in the reaction include inorganic azides such as sodium azide, barium azide and lithium azide, and organic azides such as trimethylsilyl azide and diphenylphosphoryl azide, preferably sodium azide.

The amount of the azide used is usually 0.9 to 2 mol, preferably 1 to 1.5 mol, per 1 mol of the compound (2).

A catalyst such as aluminum chloride, titanium tetrachloride or zinc chloride may be added to the reaction, and aluminum chloride is preferably used. These catalysts are usually used in an amount of 0.001 to 1 mol, preferably 0.01 to 0.5 mol, per 1 mol of the compound (2).

The mixing of the compound (2), the azide, and the catalyst is not particularly limited, but it is preferable to add the compound (2) after mixing the solvent, the catalyst, and the azide. The temperature at which the catalyst and the azide are mixed is usually −20 to 100° C., preferably −10 to 40° C.

The reaction temperature is usually 0 to 90° C., preferably 60 to 80° C. When the compound (2) is added after mixing the solvent, the catalyst, and the azide, the compound (2) is added at the above reaction temperature. The reaction time is usually 1 to 24 hours, including the time to add the compound (2).

After completion of the reaction, hydrochloric acid and an aqueous solution of sodium nitrite are added to decompose the remaining azide, and the compound (3) can be extracted with an organic solvent that is immiscible with water. The organic layer obtained by extraction may be further treated with a reducing agent such as an aqueous solution of sulfamic acid, tributylphosphine, and triphenylphosphine. Alternatively, after completion of the reaction, hydrochloric acid, sodium nitrite aqueous solution, and a tertiary phosphine compound such as tributylphosphine and triphenylphosphine are added to decompose the remaining azide, and the compound (3) is extracted with an organic solvent immiscible with water. The organic layer obtained by extraction may be further treated with a reducing agent such as an aqueous solution of sulfamic acid, tributylphosphine, and triphenylphosphine. The compound (3) can be isolated by crystallization of the compound (3) contained in the organic layer by means of concentration, cooling or/and addition of a poor solvent, followed by filtration. Alternatively, the organic layer can be used as it is, or the organic layer dehydrated by performing an operation such as azeotropic dehydration can be used in the next step.

The compound (4) can be produced by reacting the compound (3) with a methylating agent under basic conditions.

Examples of the solvent used in the reaction include hydrocarbons such as n-heptane, n-hexane, cyclohexane, n-pentane, toluene, xylene, and ethylbenzene, ethers such as diethyl ether, tetrahydrofuran, 1,4-dioxane, and ethylene glycol dimethyl ether, anisole, methyl tert-butyl ether and diisopropyl ether, halogenated hydrocarbons such as dichloromethane, 1,2-dichloroethane, tetrachloroethane, chlorobenzene and ortho-dichlorobenzene, acid amides such as N, N-dimethylformamide, 1, 3-dimethyl-2-imidazolidinone, and N-methylpyrrolidone, esters such as ethyl acetate and methyl acetate, sulfoxides such as dimethyl sulfoxide, ketones such as acetone, methyl ethyl ketone and methyl isobutyl ketone, nitriles such as acetonitrile and propionitrile, water and mixtures thereof. Preferred are N, N-dimethylformamide, acetone, methyl isobutyl ketone, toluene, xylene and ethylbenzene, and more preferably methyl isobutyl ketone, toluene, xylene and ethylbenzene.

Examples of the methylating agent include alkyl halides such as methyl bromide and methyl iodide, dialkyl sulfates such as dimethyl sulfate, alkyl sulfate esters such as methyl p-toluenesulfonate and methyl methanesulfonate, and aryl sulfate esters, and preferred is dimethyl sulfate.

Examples of the base include organic bases such as triethylamine, pyridine, 4-dimethylaminopyridine and diisopropylethylamine, alkali metal carbonates such as lithium carbonate, sodium carbonate and potassium carbonate, alkali metal hydrogen carbonates such as lithium hydrogen carbonate, sodium hydrogen carbonate and potassium hydrogen carbonate, alkali metal hydroxides such as lithium hydroxide, sodium hydroxide, and potassium hydroxide, alkali metal hydrides such as lithium hydride, sodium hydride, and potassium hydride, and alkali metal alkoxides such as sodium methoxide, sodium tert-butoxide, and potassium tert-butoxide. Preferred are potassium carbonate, sodium hydroxide and potassium hydroxide.

The amount of the methylating agent used is usually 1 to 5 mol, preferably 1 to 1.5 mol, per 1 mol of the compound (3)

The amount of the base used is usually 1 to 5 mol, preferably 1 to 1.5 mol, per 1 mol of the compound (3).

The reaction temperature is usually in the range of −20 to 150° C., preferably −5 to 30° C., and even more preferably 10 to 25° C. The reaction time is usually 1 to 24 hours.

The mixing of the solvent, the compound (3), the methylating agent, and the base is not particularly limited, but a method of adding the methylating agent after adding the base to the mixture of the compound (3) and the solvent, a method of adding a base to the mixture of the compound (3) and the methylating agent, or a method of adding the methylating agent and the base to the compound (3) at the same time is preferable. When a base soluble in water is used as an aqueous solution, it is preferably used in the presence of a phase transfer catalyst. Examples of the phase transfer catalyst include tetrabutylammonium bromide, benzyltrimethylammonium chloride, benzyltriethylammonium chloride, methyltrioctylammonium chloride and the like.

After completion of the reaction, an aqueous solution of an alkali metal hydroxide such as sodium hydroxide can be mixed to decompose the remaining methylating agent. At that time, alkyl sulfates such as sodium dodecyl sulfate may be added. After decomposing the remaining methylating agent, the compound (4) can be isolated by crystallization of the compound (4) contained in the organic layer by means of concentration, cooling or/and addition of a poor solvent, followed by filtration. The isolated compound (4) can also be further purified by chromatography, recrystallization and the like.

Hereinafter, the present invention will be described in detail with reference to Examples.

EXAMPLES

Example 1

Production of Compound (2)

In a nitrogen-flushed flask, 94.6 g of toluene, 222.4 g of water and 105.1 g of the hydrochloride salt of the compound (1) (purity 94.8%) were added successively at room temperature (pH of the aqueous layer=1.4). The mixture was brought to 5° C. and 66.9 g of phosgene gas and 222.4 g of water were added simultaneously over a period of 330 minutes (during which time the pH of the aqueous layer was less than 0.0). The resulting mixture was stirred at 5° C. for 1 hour, then 9 g of phosgene gas was added over 45 minutes and the mixture was further stirred at 5° C. for 2 hours. The resulting mixture was divided to remove the aqueous layer (theoretical hydrogen chloride concentration: 15% by weight), yielding an organic layer of 177.0 g. The content of the compound (2) contained in the organic layer was checked by HPLC analysis and found to be 46.6% by weight (yield 87.7%).

The theoretical hydrogen chloride concentration was calculated using the following method.

The weight of hydrogen chloride (stoichiometric amount) resulting from the hydrochloride salt of the compound (1) and phosgene, 80.3 g, was divided by the weight of the separated aqueous layer, 522.3 g.

Example 2

Production of Compound (2)

In a nitrogen-flushed flask, 245.2 g of toluene and 306.5 g of water were added successively at room temperature. The mixture was brought to 5° C. and 6.7 g of phosgene gas was added to the mixture over a period of 8 minutes. To the mixture obtained, 66.8 g of phosgene gas and 250.1 g of compound (1) (81.7% purity) were added over 260 minutes, each simultaneously at a uniform rate (during which time the pH of the aqueous layer was less than 0.0). To the mixture obtained, 80.2 g of phosgene gas and 237.9 g of 25% sodium hydroxide solution were added over a period of 350 minutes, each simultaneously at a uniform rate, and the mixture was then stirred for 3 hours at 5° C. (during which time the pH of the aqueous layer was less than 0.0). The resulting mixture was divided to remove the aqueous layer (theoretical hydrogen chloride concentration: 9% by weight), yielding an organic layer of 526.0 g. The content of the compound (2) contained in the organic layer was checked by HPLC analysis and was 45.1% by weight (yield 99.1%). The resulting organic layer was concentrated at 2 kPa to an internal temperature of 50° C., yielding 275.2 g of residue. The content of the compound (2) contained in the residue was checked by HPLC analysis and found to be 86.2% by weight (yield 99.1%).

The theoretical hydrogen chloride concentration was calculated using the following method.

The weight of hydrogen chloride, 59.1 g, obtained by subtracting the hydrogen chloride neutralized with sodium hydroxide from the weight of hydrogen chloride (stoichiometric amount) resulting from phosgene, was divided by the weight of the separated aqueous layer, 661.9 g.

Example 3

Production of Compounds (2), (3) and (4)

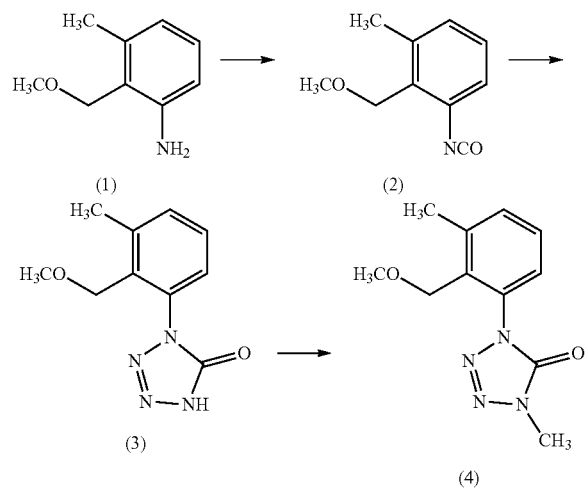

Production of Compound (2)

In a nitrogen-flushed flask, 193.7 g of toluene and 171.2 g of water were added successively at room temperature. The mixture was brought to 5° C. and 3.7 g of phosgene gas was added to the mixture over a period of 8 minutes. To the mixture obtained, 37.3 g of phosgene gas and 139.5 g of the compound (1) (81.7% purity) were added over a period of 90 minutes, each simultaneously at a uniform rate (during which time the pH of the aqueous layer was less than 0.0). To the mixture obtained, 48.5 g of phosgene gas and 144.7 g of 25% aqueous sodium hydroxide solution were added, each simultaneously and at a uniform rate, over 240 minutes, followed by stirring at 5° C. for 3 hours (during which time the pH of the aqueous layer was less than 0.0). The resulting mixture was filtered to remove the solid components and then divided to remove the aqueous layer (theoretical hydrogen chloride concentration: 9% by weight), yielding an organic layer of 349.7 g. The content of the compound (2) in the organic layer was checked by HPLC analysis and was 37.5% by weight. The resulting organic layer was concentrated under reduced pressure of 2 kPa to an internal temperature of 50° C., yielding 149.4 g of residue. The content of the compound (2) contained in the residue was checked by HPLC analysis and found to be 87.6% by weight (yield 98.0%).

The theoretical hydrogen chloride concentration was calculated using the following method.

The weight of hydrogen chloride, 33.0 g, obtained by subtracting the hydrogen chloride neutralized with sodium hydroxide from the weight of hydrogen chloride (stoichiometric amount) resulting from phosgene, was divided by the weight of the separated aqueous layer, 372.0 g.

Production of Compound (3)

In a nitrogen-flushed flask, 46 g of N,N-dimethylformamide, 1.8 g of aluminium (III) chloride and 9.6 g of sodium azide were added successively at room temperature. The resulting mixture was stirred at 75° C. for 30 minutes, after which 27.4 g of the compound (2) (purity 87.6%) was added over a period of 4 hours. After confirming the completion of the conversion to the compound (3) by HPLC analysis, the reaction mixture was cooled to 45° C. To the mixture obtained, 4.7 g of 40% sodium nitrite solution was added, followed by a dropwise addition of 21.0 g of 20% hydrochloric acid. To the mixture obtained, 120.0 g of methyl isobutyl ketone and 21.6 g of water were added successively, followed by a dropwise addition of 21.9 g of 12% aqueous sulfamic acid solution. The resulting mixture was divided to remove the aqueous layer, and the temperature of the resulting organic layer was raised to 75° C., after which 0.8 g of tributylphosphine was added dropwise and the mixture was stirred at 75° C. for 3 hours. The resulting organic layer was washed with 48.4 g of 20% brine and divided to remove the aqueous layer. The content of the compound (3) contained in the organic layer was determined by HPLC to be 27.4 g (yield 91.8%).

Production of Compound (4)

The resulting organic layer containing the compound (3), 156.7 g (concentration 17.2% by weight), was dehydrated by refluxing under reduced pressure to 18 kPa until the temperature reached 57° C. The resulting mixture was cooled to 15° C. and 21.2 g of potassium carbonate was added. To the resulting mixture, 19.3 g of dimethyl sulfate was added dropwise over a period of 3 hours and the mixture was further stirred at 15° C. for 2 hours. The resulting mixture was brought to 40° C. and then 16.2 g of 25% by weight sodium hydroxide solution, 51.3 g of water and 0.5 g of sodium dodecyl sulfate were added successively and the mixture was divided to remove the aqueous layer. The resulting organic layer was washed with 40.8 g of 20% by weight brine and the resulting organic layer was concentrated under reduced pressure. To the residue obtained, 75.6 g of hexane was added and the mixture was cooled to 0° C. The resulting solid was filtered and the obtained solid was dried under reduced pressure to give 27.2 g of the compound (4) (content 96.0 by weight, yield 90.9%).

Example 4

Production of Compounds (2), (3) and (4)
Production of Compound (2)

In a nitrogen-flushed flask, 177.0 g of toluene and 221.2 g of water were added successively at room temperature. The mixture was brought to 5° C. and 4.8 g of phosgene gas was added to the mixture over a period of 60 minutes. To the mixture obtained, at the same temperature, 28.3 g of phosgene gas and 47.8 g of the compound (1) (purity 81.9%) were added over a period of 5.1 hours, each simultaneously at a uniform rate. To the mixture obtained, at the same temperature, 77.8 g of phosgene gas, 132.2 g of the compound (1) and 171.7 g of 25% sodium hydroxide solution were added over a period of 16.7 hours, each simultaneously at a uniform rate. To the resulting mixture, 9.7 g of phosgene was added at the same temperature over a period of 2 hours, followed by stirring for 1.5 hours. To the mixture obtained, 95.9 g of water was added at the same temperature and the mixture was then stirred for 1.5 hours. The resulting mixture was divided to remove the aqueous layer (theoretical hydrogen chloride concentration: 9% by weight), yielding an organic layer of 377.0 g. The content of the compound (2) in the organic layer was checked by HPLC analysis and found to be 45.1% by weight. To the resulting organic layer was added 331.9 g of toluene and the mixture was concentrated at 7 kPa to an internal temperature of 70° C., yielding 199.0 g of residue. The content of compound (2) in the residue was checked by HPLC analysis and found to be 84.9% by weight (yield 97.7%).

The theoretical hydrogen chloride concentration was calculated using the following method.

The weight of hydrogen chloride, 49.8 g, obtained by subtracting the hydrogen chloride neutralized with sodium hydroxide from the weight of hydrogen chloride (stoichiometric amount) resulting from phosgene, was divided by the weight of the separated aqueous layer, 582.6 g.

Production of Compound (3)

In a nitrogen-flushed flask, 219.5 g of N,N-dimethylformamide, 8.3 g of aluminium (III) chloride and 42.3 g of sodium azide were added successively at room temperature. The resulting mixture was stirred at 75° C. for 30 minutes, after which 130.0 g of the compound (2) (purity 84.9%) was added over a period of 3 hours. After confirming the completion of the conversion to the compound (3) by HPLC analysis, the reaction mixture was cooled to 45° C. To the mixture obtained, 11.2 g of a 40% sodium nitrite solution and 2.6 g of tributylphosphine were added successively. To the mixture obtained, 84.8 g of 20% hydrochloric acid, 547.6 g of toluene, 86.0 g of water and 9.5 g of 20% hydrochloric acid were added successively and the aqueous layer was adjusted to pH 4.5 and stirred at 45° C. for 1 hour. To the mixture obtained, 75.0 g of 12% aqueous sulfamic acid solution and 9.5 g of 20% hydrochloric acid were added successively, and the aqueous layer was removed by separation to give 792.8 g of the organic layer. The content of compound (3) in the organic layer was determined by HPLC to be 127.7 g (yield 93.1%).

Production of Compound (4)

In a nitrogen-flushed flask, 314.4 g (concentration 16.1% by weight) of the organic layer containing the obtained compound (3) was added to bring the mixture at 16° C. To the mixture obtained, 39.2 g of toluene, 6.6 g of 50% aqueous tetrabutylammonium bromide and 1.45 g of dimethyl sulfate were added successively, followed by the simultaneous dropwise addition of 35.0 g of dimethyl sulfate and 44.2 g of 25% aqueous sodium hydroxide at 16° C. over a period of 2 hours. The resulting mixture was stirred at 16° C. for 2 hours and then the aqueous layer was removed by separation. The resulting organic layer was raised to 35° C., 19.7 g of 10% sodium hydroxide was added, the mixture was stirred for 2 hours and the aqueous layer was removed by separation. The resulting organic layer was washed with 14.6 g of water. The resulting organic layer was concentrated under reduced pressure. To the resulting residue (the concentration of the compound (4) was 37% by weight) was slowly added 91.1 g of n-hexane and the mixture was cooled to 0° C. The precipitated solid was filtered off and the residue was washed with a mixture of toluene/hexane=1/1 to give 48.8 g of the compound (4) (content 96.3% by weight, yield 87.2%).

Production of Compound (3)

In a nitrogen-flushed flask, 87.2 g of N,N-dimethylformamide, 3.3 g of aluminium (III) chloride and 16.3 g of sodium azide were added successively at room temperature. The resulting mixture was stirred at 75° C. for 30 minutes, after which 50.2 g of the compound (2) (purity 86.3%) was added over a period of 3 hours. After confirming by HPLC analysis that the conversion to the compound represented by formula (3) was complete, the reaction mixture was cooled to 45° C. To the mixture obtained, 4.4 g of a 40% sodium nitrite solution and 1.0 g of tributylphosphine were added successively. Then, 36.0 g of 20% hydrochloric acid, 172.5 g of toluene and 17.4 g of water were added successively and the aqueous layer was adjusted to have pH of 4.5 and kept warm for 1 hour. Then 29.8 g of 12% sulfamic acid solution and 4.2 g of 20% hydrochloric acid were added successively, and the aqueous layer (aqueous layer-1) and the organic layer were separated. The resulting organic layer was mixed with 35.8 g of water and 40.7 g of 25% sodium hydroxide, and the aqueous layer (aqueous layer-2) and the organic layer were separated. The resulting aqueous layer-2, aqueous layer-1, 167.2 g of toluene and 46.1 g of 20% hydrochloric acid were mixed, and after separation the organic layer, 242.5 g, was obtained. The content of the compound (3) in the organic layer was determined by HPLC to be 49.8 g (yield 92.9%).

Comparative Example 1

In a nitrogen-flushed flask, 29.5 g of toluene and 578.8 g of saturated sodium bicarbonate water were added successively at room temperature. The mixture was cooled to 5° C. and 4.0 g of a 20% by weight phosgene solution in toluene was added dropwise over 8 minutes. To the mixture obtained, 40 g of 20% by weight phosgene solution in toluene and 30 g of the compound (1) (purity 81.7%) were each added simultaneously over 190 minutes at the same temperature (pH of the aqueous layer=7.2). To the mixture obtained, 48.0 g of 20% by weight phosgene solution in toluene was added dropwise over 120 minutes at the same temperature (pH of the aqueous layer=7.1) and the mixture was then stirred for 1 hour. The resulting mixture was filtered and the residue was washed with about 90 g of toluene. The resultant filtrate and washings were combined and separated to remove the aqueous layer, yielding 125.7 g of the organic layer. The content of the compound (2) in the organic layer was checked by HPLC analysis to be 2.6% by weight (yield 11.4%).

INDUSTRIAL APPLICABILITY

According to the present invention, 3-methyl-2-(methoxymethyl)-1-isocyanatobenzene, useful as an agrochemical intermediate, can be produced in a high yield.

The invention claimed is:

1. A method for producing the compound represented by formula (2)

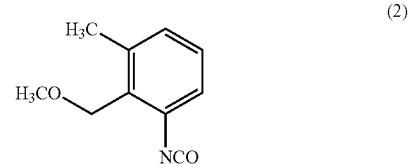

by reacting the compound represented by formula (1) with phosgenes to obtain the compound represented by formula (2), wherein, in the presence of a water-immiscible solvent and water, the compound represented by formula (1)

(1) [structure: benzene ring with H₃C, H₃CO-CH₂, and NH₂ substituents]

or its salt and the phosgenes are mixed under a condition such that an aqueous layer has a pH of 1 or less.

2. The method as claimed in claim 1, wherein the aqueous layer has a concentration of hydrogen chloride of 15% by weight or less.

3. The method as claimed in claim 2, wherein a base is added such that the aqueous layer has a concentration of hydrogen chloride of 15% by weight or less.

4. The method as claimed in claim 3, wherein the base is an alkali metal hydroxide.

5. The method as claimed in claim 1, wherein the phosgenes correspond to phosgene.

6. The method as claimed in claim 1, wherein the compound or salt thereof represented by formula (1) is a hydrochloride salt of the compound represented by formula (1).

7. The method as claimed in claim 1, further comprising a step of separating a mixture of an organic layer containing the compound represented by formula (2) and the aqueous layer obtained by the reaction to obtain the organic layer containing the compound represented by formula (2), and a step of dehydrating the organic layer at 50° C. or lower.

8. A method for producing a compound represented by formula (3)

(3) [structure: aryl tetrazolinone]

comprising the following steps:

Step 1 of producing the compound represented by formula (2)

(2) [structure: benzene ring with H₃C, H₃CO-CH₂, and NCO substituents]

by reacting the compound represented by formula (1)

(1) [structure: benzene ring with H₃C, H₃CO-CH₂, and NH₂ substituents]

with phosgenes to obtain the compound represented by formula (2), wherein, in the presence of a water-immiscible solvent and water, a salt of the compound represented by formula (1), phosgenes and an alkali metal hydroxide are mixed under a condition such that an aqueous layer has a pH of 1 or less and the aqueous layer has a concentration of hydrogen chloride of 15% by weight or less;

Step 2 of obtaining an organic layer containing the compound represented by formula (2) from the mixture of an organic layer containing the compound of formula (2) and an aqueous layer obtained in Step 1, and dehydrating the organic layer at 50° C. or lower; and Step 3 of reacting the compound represented by formula (2) obtained in step 2 with an azide.

9. A method for producing a compound of formula (4)

(4) [structure: N-methylated aryl tetrazolinone]

comprising, in addition to the Step 1, the Step 2 and the Step 3 recited in claim 8, a further step of methylating the obtained compound of formula (3).

* * * * *